(12) United States Patent
Landini et al.

(10) Patent No.: US 6,287,760 B1
(45) Date of Patent: Sep. 11, 2001

(54) WESTERN BLOT TEST FOR THE IDENTIFICATION OF ANTIBODIES SPECIFIC AGAINST THE HCMV VIRUS

(75) Inventors: Maria P. Landini, Bologna (IT); Gregory T. Maine, Gurnee, IL (US); Alessandro Ripalti, Bologna; Tiziana Lazzarotto, Bolzano, both of (IT)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/242,391

(22) PCT Filed: Aug. 7, 1997

(86) PCT No.: PCT/US97/13942

§ 371 Date: Jul. 8, 1999

§ 102(e) Date: Jul. 8, 1999

(87) PCT Pub. No.: WO98/07033

PCT Pub. Date: Feb. 19, 1998

(30) Foreign Application Priority Data

Aug. 16, 1996 (IT) .............................................. TO96A0705

(51) Int. Cl.⁷ ...................................................... C12Q 1/70

(52) U.S. Cl. .............................. 435/5; 436/518; 530/350

(58) Field of Search .................... 435/5, 320.1; 530/350; 436/518

(56) References Cited

U.S. PATENT DOCUMENTS 5,124,255  6/1992  Boling et al. .

FOREIGN PATENT DOCUMENTS

| 4426453 | 11/1995 | (DE) . |
| 0263025 | 4/1988 | (EP) . |
| 0301141 | 2/1989 | (EP) . |
| 0397129 | 11/1990 | (EP) . |
| 0534102 | 3/1993 | (EP) . |
| WO 92/00323 | 1/1992 | (WO) . |
| WO 96/01321 | 1/1996 | (WO) . |
| WO 96/36722 | 11/1996 | (WO) . |

OTHER PUBLICATIONS

Gold, D. et al. "Immunoblot Analysis of the Humoral Immune Response in Primary Cytomegalovius Infection", Feb. 1988, vol. 157, No. 2, pp 319–325.
Lazzarotto, et al. "Enzyme–Linked Immunoadsorbent Assay for the Detection of Cytomegalovirus–Igm: Comparison Between Eight Commercial Kits, Immunofluorescence, and Immunoblotting", Journal of Clinical Laboratory Analysis, vol. 6, (1992), pp. 216–218.
Bankier, et al., "The DNA sequence of the human cytomegalovirus genome", J. DNA Sequencing & Mapping, vol. 2, (1991), pp. 1–12.
Battista, et al., "Intracellular production of a major cytomegalovirus antigenic protein in the methylotrophic yeast Pichia pastoris" GENE vol. 176, (1996), pp 197–201.
Chee, et al., "Analysis of the Protein–Coding Content of the Sequence of Human Cytomegalovirus Strain AD169", Current Topics in Microbiology and Immunology, vol. 154, (1990), pp. 26–167.
Gleaves, et al., "Rapid Detection of Cytomegalovirus in MRC5 Cells Inoculated with Urine Specimens by Using Low–Speed Centrifugation and Monoclonal Antibody to an Early Antigen", Journal of Clinical Microbiology, vol. 19, No. 6, (1984), pp. 917–919.
Keesler, et al., "The Binding Activity of the Macrophage Lipoprotein (a)/Apolipoprotein (a) Receptor is Induced by Cholesterol via a Post–translational Mechanism and Recognizes Distinct Kringle Domains on Apolipoprotein (a)*", The Journal of Biological Chemistry, vol. 271, No. 50, (1996), pp. 32096–32104.
Klezovitch, et al. "Heterogeneity of lipoprotein (a) growing complexities", Current Opinion in Lipidology, vol. 6, (1995), pp. 223–228.
Labeur, et al. "Methods for the measurement of lipoprotein (a) in the clinical laboratory", Current Opinion in Lipidology, vol. 3, (1992), pp. 372–376.
Lackner, et al., "Molecular definition of the extreme size polymorphism in apolipoprotein (a)", Human Molecular Genetics, vol. 2, No. 7, (1993), pp. 933–940.
Lafferty, et al., "Immunochemistry of human Lp[a]: characterization of monoclonal antibodies that cross–react strongly with plasminogen", Journal of Lipid Research, vol. 32, (1991), pp. 277–292.
Landini, et al., "Reactivity of cytomegalovirus structural polypeptides with different subclasses of IgG present in human serum", Journal of Infection, vol. 16(2), (1988), pp. 163–167.
Landini, et al., "Human Immune Response to Cytomegalovirus Structural Polypeptides Studied by Immunoblotting", Journal of Medical Virology, vol. 17, (1985), pp. 303–311.
Lazzarotto, et al., "Detection of Serum Immunoglobulin M to Human Cytomegalovirus by Western Blotting Correlates Better with Virological Data than Detection by Conventional Enzyme Immunoassay", Clinical and Diagnostic Laboratory Immunology , vol. 3, No. 5, (1996), pp. 597–600.

(List continued on next page.)

Primary Examiner—Donna C. Wortman
(74) Attorney, Agent, or Firm—David L. Weinstein

(57) ABSTRACT

Diagnostic tool for the identification of anti-HCMV antibodies in human serum. The tool comprises a means of solid support having two sections, a first section bearing a plurality of HCMV proteins (vp) obtained from purified virions concentrated in separate bands forming a predetermined pattern, one of these bands being pp 150 of HCMV; a second section bearing recombinant fusion proteins as controls, at least one band comprising a recombinant fusion protein carrying at least one epitope of pp 150.

15 Claims, 12 Drawing Sheets

OTHER PUBLICATIONS

Li, et al. "Expression and Purification of Kringle 4–Type 2 of Human Apolipoprotein (a) in *Escherichia Coli*", Protein Expression and Purification, vol. 3, (1992), pp. 212–222.

Maine, et al., "The DNA–Binding Protein pUL57 of Human Cytomegalovirus: Comparison of Specific Immunoglobulin M (IgM) Reactivity with IgM Reactivity to Other Major Target Antigens", Clinical & Diagnostic Laboratory Immunology, vol. 3, No. 3, (1996), pp. 358–360.

Marcovina, et al., "Effect of the Number of Apolipoprotein(a) Kringle 4 Domains on Immunochemical Measurements of Lipoprotein(a)", Clinical Chemistry, vol. 41, No. 2, (1995), pp. 246–255.

Marcovina, et al., "Structure and metabolism of lipoprotein (a)", Current Opinion in Lipidology, vol. 6, (1995), pp. 136–145.

McLean, et al. "cDNA sequence of human apolipoprotein (a) is homologous to plasminogen", Nature, vol. 330, (Nov. 12, 1987), pp. 132–137.

Mocarski, et al., "Precise localization of genes on large animal virus genomes: Use of λgt11 and monoclonal antibodies to map the gene for a cytomegalorivus protein family", Proc. Nat'l. Acad. Sci., vol. 82, (1985), pp. 1266–1270.

Nielsen, et al., "An Enzyme Labelled Nuclear Antigen Immunoassay for Detection of Cytomegalovirus IgM Antibodies in Human Serum: Specific and Non–specific Reactions", Journal of Medical Virology, vol. 22, (1987), pp. 67–76.

Rainwater, et al. "Immunochemical characterization and quantitation of lipoprotein (a) in baboons", Atherosclerosis, vol. 73, (1988), pp. 23–31.

Revello, "Correlation Between Immunofluorescent Detection of Human Cytomegalovirus Immediate Early Antigens in Polymorphonuclear Leukocytes and Viremia", The Journal of Infectious Diseases, vol. 160, No. 1, (Jul. 1989), pp. 159–160.

Robinson, et al., "Analysis of the Humoral Response to the Flagellin Protein of *Borrelia burgdorferi*: Cloning of Regions Capable of Differentiating Lyme Disease from Syphilis", Journal of Clinical Microbiology, vol. 31, No. 3, (1993), pp. 629–635.

van der Biji, et al., "Rapid Immunodiagnosis of Active Cytomegalovirus Infection by Monoclonal Antibody Staining of Blood Leukocytes", Journal of Medical Virology, vol. 25, (1988), pp. 179–188.

van der Hoek, et al., "The apolipoprotein(a) kringle IV repeats which differ from the major repeat kringle are present in variably–sized isoforms", Human Molecular Genetics, vol. 2, No. 4, (1993), pp. 361–366.

Vornhagen, et al., "The DNA–Binding Protein pUL57 of Human Cytomegalovirus Is a Major Target Antigen for the Immunoglublin M Antibody Reponse during Acute Infection", Journal of Clinical Microbiology, vol. 33, No. 7, (1995), pp. 1927–1930.

FIG. 3
TABLE 1

| COMBINATION OF REACTIVE PROTEINS WITH IGM IN SERA FROM BLOOD DONORS | | NUMBER OF SERA WITH POSITIVE REACTION | | |
|---|---|---|---|---|
| VIRAL PROTEINS | RECOMBINANT PROTEINS | FROM THE USA NUMBER = 300 | FROM ITALY NUMBER = 200 | TOTAL NUMBER-(%) |
| VP150 | | 3 | 11 | 14 (2.8) |
| VP82 | | | 3 | 3 (0.6) |
| VP38 | | | 2 | 2 (0.4) |
| VP150, VP38 | | | 2 | 2 (0.4) |
| VP150, VP82 | | 1 | 1 | 2 (0.4) |
| VP150, VP65 | | 1 | | 1 (0.2) |
| VP150, VP38, VP28 | | 1 | | 1 (0.2) |
| | RP150 | 2 | 1 | 3 (0.6) |
| | RP52 | 3 | | 3 (0.6) |
| | RP150, RP52, RP130 | 3 | | 3 (0.6) |
| | RP150, RP130 | | 2 | 2 (0.4) |
| VP150 | RP150, RP130 | 3 | | 3 (0.6) |
| VP150 | RP150 | 1 | | 1 (0.2) |
| VP150 | RP150, RP52, RP130 | 1 | | 1 (0.2) |
| VP38 | RP150 | | 1 | 1 (0.2) |
| VP150, VP82 | RP150, RP130 | | 1 | 1 (0.2) |
| VP150, VP38, VP28 | RP150, RP130 | 1 | | 1 (0.2) |
| VP150, VP38, VP28 | RP150, RP52, RP130 | 1 | | 1 (0.2) |

FIG. 4A-1

TABLE 2

| PATIENT | ANTI-GENEMIA | EIA-IgM (BEHRING) | COMBO-WB VIRAL PROTEINS | | | | | COMBO-WB RECOMBINANT PROTEINS | | | | |
|---|---|---|---|---|---|---|---|---|---|---|---|---|
| | | | P150 | P82 | P65 | P38 | P28 | 1A | 5A | 57C | CKS | μ |
| FIO (HTR.R-) | | | | | | | | | | | | |
| 12.4.94 | - | 0.007 | - | - | - | - | - | - | - | - | - | + |
| 5.5.94 | 3 | 0.011 | - | - | - | - | - | - | - | - | - | + |
| 10.5.94 | 135 | 0.011 | - | - | - | - | - | - | - | - | - | + |
| 12.5.94 | 30 | 0.052 | - | - | - | - | - | - | - | - | - | + |
| 19.5.94 | 1 | 0.370 | - | - | - | - | - | - | - | - | - | + |
| 2.6.94 | 2 | 0.279 | - | - | - | - | - | - | - | - | - | + |
| 16.6.94 | - | 0.472 | - | + | - | - | - | + | - | - | - | + |
| 28.6.94 | 17 | 0.885 | + | + | - | - | - | + | - | - | - | + |
| 7.7.94 | 3 | 1.050 | + | + | - | - | - | + | - | - | - | + |
| 28.9.94 | - | 0.104 | ++ | - | - | - | - | +++ | - | +++ | - | + |
| 25.10.94 | - | 0.135 | ++ | - | - | - | - | +++ | - | +++ | - | + |
| ARQ (HTR.R-) | | | | | | | | | | | | |
| 22.11.94 | - | 0.087 | - | - | - | - | - | - | - | - | - | + |
| 6.12.94 | - | 0.075 | - | - | - | - | - | - | - | - | - | + |
| 13.12.94 | 6 | 1.407 | - | - | + | ++ | - | + | + | + | - | + |
| 22.12.94 | - | >2.0 | + | - | ++ | ++ | + | + | + | + | - | + |
| 16.1.95 | 50 | 1.678 | + | - | + | ++ | ++ | + | + | + | - | + |
| 20.2.95 | - | 1.477 | - | - | - | + | + | - | - | - | - | + |
| BOS (HTR.R-) | | | | | | | | | | | | |
| 8.11.94 | - | 0.000 | - | - | - | - | - | - | - | - | - | + |
| 21.11.94 | 59 | 0.023 | - | - | - | - | - | - | - | - | - | + |
| 30.11.94 | - | 0.537 | + | + | - | + | - | ++ | ++ | ++ | - | + |
| 13.12.94 | - | 0.607 | ++ | + | - | + | + | ++ | ++ | ++ | - | + |
| 10.1.95 | - | 0.573 | ++ | + | - | ++ | - | ++ | ++ | ++ | - | + |
| 26.1.95 | - | 0.907 | ++ | - | + | ++ | - | ++ | ++ | ++ | - | + |

FIG. 4A-2

TABLE 2–(CONTINUED)

| PATIENT | ANTI-GENEMIA | EIA-IgM (BEHRING) | COMBO-WB ||||||||||
|---|---|---|---|---|---|---|---|---|---|---|---|---|
| | | | VIRAL PROTEINS ||||| RECOMBINANT PROTEINS |||||
| | | | P150 | P82 | P65 | P38 | P28 | 1A | 5A | 57C | CKS | μ |
| FIR (HTR.R+) | | | | | | | | | | | | |
| 27.94 | – | 0.149 | – | – | – | – | – | – | – | – | – – | + |
| 24.11.94 | 74 | 0.524 | + | – | – | + | + | + | – | + | – | + |
| 17.11.94 | 67 | 0.627 | + | – | – | + | + | + | – | + | – | + |
| 22.11.94 | 10 | 0.539 | + | – | – | + | + | + | – | + | – | + |
| 7.12.94 | – | 0.296 | + | – | – | + | – | – | – | – | – | + |
| 23.2.95 | – | 0.229 | + | – | – | + | – | – | – | – | – | + |
| 23.3.95 | – | 0.129 | + | – | – | + | – | – | – | – | – | + |
| 22.4.95 | – | 0.108 | + | – | – | – | – | – | – | – | – | + |
| 7.6.95 | – | 0.145 | + | – | – | – | – | – | – | – | – | + |
| CIC (HTR.R+) | | | | | | | | | | | | |
| 7.7.94 | – | 0.114 | – | – | – | – | – | – | – | – | – | – |
| 12.7.94 | – | 0.080 | – | – | – | – | – | – | – | – | – | + |
| 21.7.94 | 7 | 0.247 | – | – | – | +++ | + | – | – | – | – | + |
| 26.7.94 | 5 | 0.593 | + | – | – | +++ | ++ | – | + | – | – | + |
| 11.8.94 | – | 0.772 | + | + | + | +++ | ++ | – | + | – | – | + |
| 26.9.94 | – | 0.402 | + | + | + | +++ | ++ | – | + | – | – | + |
| 10.11.94 | – | 0.431 | + | + | + | +++ | ++ | – | + | – | – | + |

FIG. 4B-1

TABLE 2-(CONTINUED)

| PATIENT | ANTI-GENEMIA | EIA-IgM (BEHRING) | COMBO-WB ||||||||||
|---|---|---|---|---|---|---|---|---|---|---|---|---|
| | | | VIRAL PROTEINS ||||| RECOMBINANT PROTEINS ||||| 
| | | | P150 | P82 | P65 | P38 | P28 | 1A | 5A | 57C | CKS | μ |
| SAB (HTR.R+) | | | | | | | | | | | | |
| 15.11.93 | – | 0.010 | – | – | – | – | – | – | – | – | – | + |
| 22.11.93 | – | 0.007 | – | – | – | – | – | – | – | – | – | + |
| 28.11.93 | – | 0.002 | – | – | – | – | – | – | – | – | – | + |
| 14.12.93 | – | 0.036 | – | – | – | – | – | – | – | – | – | + |
| 12.1.94 | 229 | 0.120 | + | + | – | – | – | + | – | + | – | + |
| 17.1.94 | 369 | 0.157 | + | + | – | – | + | + | – | + | – | + |
| 19.1.94 | 159 | 0.440 | + | + | – | – | + | + | – | + | – | + |
| 24.1.94 | 10 | 0.784 | + | + | – | – | + | ++ | – | ++ | – | + |
| 9.2.94 | – | 0.996 | + | + | – | + | ++ | ++ | + | ++ | – | + |
| 2.3.94 | – | 0.865 | + | + | – | – | + | ++ | + | ++ | – | + |
| | | | | | | | | | | | | |
| BAT (RTR.R–) | | | | | | | | | | | | |
| 23.11.92 | – | 0.009 | – | – | – | – | – | – | – | – | – | + |
| 22.12.92 | – | nd | – | – | + | – | – | – | – | – | – | + |
| 21.1.93 | 45 | 0.697 | + | – | ++ | – | – | – | + | – | nd | nd |
| 3.2.93 | 21 | 0.668 | + | – | ++ | – | – | – | + | – | – | + |
| 10.2.93 | 11 | 0.425 | + | – | ++ | – | – | – | + | – | – | + |
| 24.2.93 | nd | 0.415 | + | – | + | – | – | – | + | – | – | + |
| 5.3.93 | 2 | nd | + | – | + | – | – | – | + | – | – | + |
| | | | | | | | | | | | | |
| FER (RTR.R–) | | | | | | | | | | | | |
| 5.8.91 | – | 0.000 | – | – | – | – | – | – | – | – | – | + |
| 9.9.91 | ND | 0.021 | – | – | – | – | – | – | – | – | – | + |
| 16.9.91 | 1520 | 0.470 | + | + | – | – | + | ++ | – | ++ | – | + |
| 8.10.91 | – | 0.557 | + | + | – | – | + | ++ | – | ++ | – | + |
| 20.11.91 | 2 | 0.561 | + | + | – | + | + | ++ | – | ++ | – | + |

FIG. 4B-2

TABLE 2–(CONTINUED)

| PATIENT | ANTI-GENEMIA | EIA–IgM (BEHRING) | COMBO–WB ||||||||||
|---|---|---|---|---|---|---|---|---|---|---|---|---|
| | | | VIRAL PROTEINS ||||| RECOMBINANT PROTEINS |||||
| | | | P150 | P82 | P65 | P38 | P28 | 1A | 5A | 57C | CKS | $\mu$ |
| CUP (HTR.R+) | | | | | | | | | | | | |
| 29.8.95 | – | 0.046 | – | – | – | + | – | – | – | – | – | + |
| 5.9.95 | – | 0.030 | – | – | – | + | – | – | – | – | – | + |
| 14.9.95 | – | 0.060 | + | + | – | + | + | + | + | + | – | + |
| 3.10.95 | 14 | 0.007 | + | + | – | + | + | + | + | + | – | + |
| 19.10.95 | 780 | 0.365 | + | + | – | + | + | + | + | + | – | + |
| 25.10.95 | – | 0.537 | + | + | – | + | + | + | + | + | – | + |
| 7.11.95 | 2 | 0.476 | + | + | – | + | + | + | + | + | – | + |
| 16.11.95 | 5 | 0.531 | + | + | – | + | + | + | + | + | – | + |
| 6.12.95 | – | 0.436 | + | + | – | + | – | + | + | + | – | + |
| | | | | | | | | | | | | |
| | | | | | | | | | | | | |
| MAR (RTR.R+) | | | | | | | | | | | | |
| 25.11.92 | nd | 0.018 | – | – | – | – | – | – | – | – | – | + |
| 28.12.92 | nd | 0.380 | + | + | + | ++ | + | ++ | – | ++ | – | + |
| 2.2.93 | 20 | 0.235 | + | – | + | + | – | ++ | – | ++ | – | + |
| 10.2.93 | 3 | 0.314 | + | – | + | + | – | ++ | – | ++ | – | + |

FIG. 5

TABLE 3

| GROUP OF SUBJECTS | NUMBER OF SERA | NUMBER OF POSITIVE SAMPLES FOR ANTI-HCMV IgM | |
|---|---|---|---|
| | | EIA TEST | COBO WB |
| RECIPIENTS OF HEART TRANSPLANTS PCR POSITIVE IN PMLN | 85 | 39 | 58 |
| WOMEN IN PREGNANCY WITH ACTIVE INFECTIONS | 38 | 22 | 34 |

FIG. 6

| 1 | 2 | 3 | 4 | 5 | 6 | 7 | |
|---|---|---|---|---|---|---|---|
| — | — | — | | — | | | –VP 150 |
| | ▬ ▬ | | | | | | –VP 82 |
| █ | █ | | | | | | ]–VP 65 |
| | ▬ | | | | | | |
| | | | | | | | |
| — | ▬ | ▬ | ■ | — | | | –VP 38 |
| | | | | | | | ]–VP 28 |
| ▬ | ▬ | ▬ | | ▬ | | | –RP 150 |
| ▬ | ▬ | | | ▬ | | | –RP 52 |
| ▬ | ▬ | ▬ | | ▬ | | | –RP 130 |
| | | | | | | | –CKS |
| = | = | = | = | = | = | | –$\mu$ |

FIG. 8

VIRAL AGENTS
- VP 150
- i₄
- VP 82
- i₃
- VP 65
- i₂
- VP 38
- i₁
- VP 28

RECOMBINANT AGENTS
- RP 150
- e₂
- RP 52
- e₁
- RP 130

CKS
μ

WESTERN BLOT TEST FOR THE IDENTIFICATION OF ANTIBODIES SPECIFIC AGAINST THE HCMV VIRUS

The present invention relates to a diagnostic tool for the identification in human serum of specific antibodies against Human Cytomegalovirus (HCMV); the present invention relates, in addition, to an improved form of the Western blot test for the identification of anti-HCMV antibodies which makes use of the said diagnostic tool, with the said test having a heightened level of reliability and therefore being able to be taken as an advantageous standard of reference in the serological control of the results of a first test which is carried out by means of traditional techniques, such as the Enzymatic Immune Analysis (EIA), as well as to represent a test which stands alone for the search for anti-HCMV antibodies. The invention relates, in addition, to a method of identification in the human serum of the specific IgM and/or IgG and/or IgA of Cytomegalovirus by using the said improved Western Blot test. The invention relates, finally, to the recombinant fusion proteins which are used, along with other viral antigens which are obtained from purified virions, in the said method, and to the plasmids which express the said proteins.

HCMV is a ubiquitous agent of infection in the human. It is rarely pathogenic in healthy adults, but it is associated with various disorders in immune-depressed individuals. In addition, HCMV is the most common cause of congenital infections in the human, and primary maternal infections are second only to Down's Syndrome as a known cause of mental retardation in the neonate [2].

The serological diagnosis of infections from HCMV is carried out, as a general rule, by by means of the enzymatic immune test (EIA), which uses as the antigenic material either the virus itself, purified to various levels, or else lysates of the infected cells. The various commercial kits which are currently available on the market for carrying out such tests, however, can not be referred to any standard and, for that reason, the results which they supply are frequently in little agreement with one another, with some being too specific and insufficiently sensitive, while others are too sensitive and insufficient specific [6], thus yielding, on the whole, a large number of responses which are falsely positive or falsely negative.

It is well known, in this connection, that the serological analysis which is carried out by means of the "Western blot" method, even though it is much more expensive and requires longer time in comparison with the EIA test, is still much more reliable than the latter, most particularly in regard to the specificity of the final result. This is the reason, among others, that, in the event of infections from HIV, a Western blot test (frequently referred to as "WB") is always used to confirm a doubtful EIA test.

The most effective antigenic substance for the serological investigation of HCMV is certainly the virus itself. In the procedure in accordance with the traditional Western blot test, the virus is, after the purification of the cultures of infected cells, suspended in a denaturing mixture and its structural proteins are fractionated in preparatory gels of polyacrylamide. The typical pattern of proteins which is thus generated is then transferred to a solid support (which is, as a general rule, nitrocellulose); the spots ("blots") which are thus obtained are successively sub-divided into various strips of a few millimeters of width: each strip is then assayed with the serum which is to be examined.

The WB test is not entirely free of disadvantages, however: in the first place, the structural antigen of the HCMV virus which is provided with the highest immunogenic capacity, against which the longest-last immunological response is produced, is a polypeptide with the molecular weight of 150 kD (coded by the gene UL32 of the virus itself, and referred to as ppUL32). This polypeptide, as a general rule, migrates in the polyacrylamide gel along with another structural component of the HCMV virus (coded by the gene UL86 and referred to as ppUL86), which has the same molecular weight and, although it is a relatively effective immunogenic substance, it is only scantily specific, because it includes antigenic epitopes in common with the homologous proteins of the other viruses of the family Herpesviridae, and is thus to be defined a "group antigen". As the result, in the relatively frequent case in which the band of 150 kD turns out to be the only reactive band shown of a WB test, it is not possible to stabilize (at least to a sufficient extent) if the subject who is under examination has direct antibodies against the specific antigen pp150 or against the antigen of the non-specific ppUL86 group, so that the result consequently remains equivocal [11].

In the second place, the blots which are obtained from the viral proteins (vp) do not contain the non-structural viral proteins, some of which are very strong immunogenic substances. For example, the direct antibodies against such proteins, particularly those which are directed against the phosphoprotein of 52 kD (coded by the gene UL44 of the genome of HCMV) have particular relevance, because their presence allows the serological identification of the primary infection, on the condition that the presence of these antibodies is accompanied by a weak reaction against the principal structural antigen pp150.

It would be desirable, therefore, to supply a diagnostic tool which can be used in an improved Western blot test for the identification of specific antibodies of HCMV in the human serum, which is free of the disadvantages which have been described above and, in particular, is both specific and sensitive enough to be able to constitute an advantageous standard of reference ("golden reference standard"). It would be desirable, in addition, to provide a Western blot test which is improved for the identification of the IgM's which are specific for HCMV in the human serum.

It would also be desirable to provide a method for identifying the immunoglobulins IgM and/or IgG and/or IgA which are specific for HCMV in the human serum with an increased level of reliability, in such a manner that it is possible to recognize even those results which are falsely positive or negative.

It would also be desirable to supply the recombinant protein materials which are to be used in the test and in the WB method in accordance with the invention itself.

Finally, it would be further desirable to supply plasmids which are able to be inserted into prokaryotic and/or eukaryotic host organisms, in order to thereby to express such recombinant protein materials, particularly those which are fused with the protein CKS.

In accordance with the present invention, there is therefore provided a diagnostic tool for the identification of antibodies against HCMV in the human serum, with the said diagnostic tool comprising a means for solid support, a first section of which bears a plurality of viral proteins (vp) which have been obtained from purified virions, the said viral proteins being concentrated in corresponding bands and with the bands being supported by the said first section of the solid support, spaced one from the other in accordance with a predetermined pattern; with one of the said bands being formed by at least one viral protein of approximately 150 kD molecular weight; with the said diagnostic tool being characterized in that:

(i) The said means of solid support comprises, in addition, a second section which contains a plurality of bands spaced among themselves in accordance with a predetermined pattern, with at least one first band of this second section including a single recombinant protein (rp) which comprises a first region reproducing a sequence of amino acids corresponding to at least one epitope of the viral protein pp150, and a second region reproducing at least a portion of the sequence of amino acids of an exogenous protein, which may be expressed in a prokaryotic or a eukaryotic host organism;

(ii) At least one second band of the second section includes a recombinant protein which comprises a first region reproducing a sequence of amino acids corresponding to at least one immunogenic epitope of a first non-structural protein of the HCMV virus, and a second region reproducing at least a portion of the sequence of amino acids of the said exogenous protein; and:

(iii) At least one control band formed by the said exogenous protein.

In particular, the said recombinant protein which is included in the said first band of the second section comprises the said first region, which reproduces a sequence of amino acids (F3) corresponding to at least a portion of the sequence between aa1006 and aa1048, inclusive, read in the direction from the aminic end to the carboxylic end, of the viral protein pp150; and, a third region, reproducing a sequence of amino acids (A1C2) corresponding to at least a portion of the sequence between aa595 and aa614, inclusive, read in the direction from the aminic end to the carboxylic end, of the said viral protein pp150; with the said regions being able to be variously positioned, one in relation to the other, within the said first recombinant protein.

In addition, the second band of the second section includes a recombinant protein, the said first region of which reproduces a sequence of amino acids (H10) corresponding to at least a portion of the sequence between aa202 and aa434, inclusive, read in the direction from the aminic end to the carboxylic end, of the viral protein pp52.

In accordance with one preferred form of implementation of the invention which is specifically intended to reveal the anti-HCMV IgM, the second section also comprises, in addition to a second control band comprising aliquots of the heavy $\mu$ chains, two additional recombinant proteins positioned in at least one band: the first of these comprises a first region reproducing a sequence of amino acids corresponding to at least a portion of the sequence between aa540 and aa601, inclusive, read in the direction from the aminic end to the carboxylic end, of the viral protein p130; and, at least one second region reproducing at least a portion of the sequence of amino acids of the exogenous protein; the second comprises a first region, reproducing a sequence of amino acids corresponding to at least a portion of the sequence between aa1144 and aa1233, inclusive, read in the direction from the aminic end to the carboxylic end, of the viral protein p130; and, at least one second region reproducing at least a portion of the sequence of amino acids of the exogenous protein; the said regions of the said recombinant proteins being able to be variously positioned, one in relation to the other, within each recombinant protein.

The said exogenous protein is preferably CKS and the said recombinant proteins comprise, in the said regions, the entire amino acid sequence for each of the pp52, pp150 and p130, with the said sequences of viral proteins being incorporated into the CKS, in a position which is immediately adjacent to the position aa171 of the latter.

In this way, an improved Western blot test which is carried out by making use of the diagnostic tool in accordance with the invention resolves all of the disadvantages of the known tests which are available on the market. On the one hand, the simultaneous presence on the said means of solid support of the viral protein pp150 and of a corresponding recombinant fusion protein, comprising the two most immunogenic sequences of the pp150 bound to a protein vector, makes it possible to overcome the possible non-specificity of a direct response against the band of 150 kD only. On the other hand, the lack of non-structural viral proteins among those which are derived from the purified virions is overcome by means of the insertion, into the second section of the tool, of one or more (in the specific case, another three) recombinant proteins (bound to the protein vector CKS) containing the strongest immunogenic epitopes of some of the non-structural proteins of the HCMV virus, specifically, the sequence H10 (aa202–aa434) of the pp52 and, in order to optimize the determination of the IgM's, the sequences between aa540 and aa601, and between aa1144 and aa1233 of p130 (coded by the UL57).

The basis for the present invention must consequently be seen in the combination, within the same diagnostic tool, of two sections of bands: the bands which constitute the first section are obtained in the traditional manner from purified virions, while those which constitute the second section are formed exclusively from recombinant proteins, which include within their structure strongly determinant antigens of viral proteins suitably selected, with this being for the objective of allowing a cross-checking between the responses of the two sections: the improved WB test in accordance with the invention is, for this reason, called the "Combo WB" test.

In addition, in order to prevent responses which are falsely positive or falsely negative, two control bands are inserted into the recombinant section. The first is formed by the same protein which is used as a protein vector in all of the fusion recombinant proteins of the test, in this specific case, the protein CKS: a positive response of this band will indicate the presence of anti-CKS antibodies in the serum examined and will, as the result, probably show a false positive; in a similar manner, a negative response in the band which is formed by the $\mu$ chains will show an error in the carrying out of the test and will, for that reason, yield a false negative.

From what has been described above, even if such a possibility has still not been verified by experimental means, it does appear probable that Western blot tests can easily be carried out in accordance with the invention, directed even- at the specific identification of IgG or IgA, which assure the same excellent results of the test for the IgM which is being examined. For this objective it would be sufficient, for example, to substitute the band which is formed by the recombinant protein comprising the immunogenic sequence of p130 with other recombinant proteins, always fused with the CKS, appropriately selected, particularly a recombinant protein comprising portions of the viral protein gB (expressed by the gene UL55) or of the viral protein p28 (expressed by the gene UL99); obviously, in this case, the heavy chains of class $\mu$ in the second control band would be substituted by chains of class $\gamma$ or $\alpha$, respectively.

More in general, therefore, the second section of the solid support supports at least one third band including at least one recombinant protein which includes a first region reproducing a sequence of amino acids corresponding to at least one epitope of a second protein of HCMV, either structural or non-structural, and a second region reproducing at least a portion of the sequence of amino acids of the exogenous protein; with the said second viral protein, structural or non-structural, being selected in relation to the class of antibodies which the diagnostic tool is to reveal, specifically, IgM, IgG or IgA. In this case, the said second section of the support comprises, in addition, a second control band comprising aliquots of heavy chains of a class of human immunoglobulins appropriately selected from the group of the heavy chains, $\mu$, $\gamma$ and $\alpha$.

The means for solid support is, as a general rule, constituted by a strip or by a sheet of nitrocellulose on which the viral proteins (vp) and the recombinant proteins (rp) are placed, typically adsorbed, in accordance with a predetermined pattern.

For example, the said pattern could correspond to the typical pattern of electrophoretic fractionation in polyacrylamide gel.

The typical diagnostic tool in accordance with the preferred form of implementation of the invention, which is specifically intended for the identification of the specific IgM's of the HCMV virus, comprises at least the viral proteins vp150, vp82, vp65, vp38 and vp28, with the said viral proteins having been obtained from purified virions; a plurality of recombinant proteins comprising immunogenic regions of the viral proteins pp150 and pp52 and, preferably, of pp130 (or other non-structural proteins which have been obtained by recombinant means), with the said regions being incorporated into CKS; the CKS protein, by itself; and, the heavy $\mu$ chains of the human immunoglobulins; all of these protein materials are supported by means of a solid support of nitrocellulose which is, for example, adsorbed onto this.

In accordance with another aspect of the invention, this relates to a method for the identification in the specific human serum of the IgM and/or IgG and/or IgA of HCMV, with the said method comprising the phases of:

Purifying the virions of HCMV and separating from the said purified virions at least the viral proteins vp150, vp82, vp65, vp38 and vp28;

Obtaining, preferably by means of the techniques of genetic engineering, a plurality of recombinant proteins which are able to be expressed in a host organism, with the said recombinant proteins comprising immunogenic regions of viral proteins, either structural or non-structural, and at least one region of an exogenous protein which is able to be expressed in the said organism; at least one of the said immunogenic regions of the structural or non-structural viral proteins being selected for its capacity to stimulate specific immune responses in IgM and/or IgG and or IgA;

Placing on a means of solid support the said viral proteins and the said recombinant proteins, which are spaced one from one another and positioned in accordance with a predetermined pattern;

Placing on the said means of solid support the said exogenous protein and the aliquots of heavy $\mu$ and/or $\gamma$ and/or $\alpha$ chains of human immunoglobulins, also spaced one from another and from the said viral proteins and the said recombinant proteins;

Incubating the said means of solid support, the said proteins and heavy chains of immunoglobulins being contained on this, with the human serum to be examined and with the substance of the antibodies being sought (for example, conjugates with peroxidase or other marked enzymes); and;

Comparing the consequent reaction with the viral protein and the recombinant proteins, considering the test positive only when at least one viral protein and at least one recombinant protein react simultaneously with the serum which is under examination, while the said exogenous protein does not react; with the test being repeated if the heavy chain of immunoglobulin does not react.

The present invention relates, in addition, to two plasmids, which are referred to as pCMV-30 and pCMV-31, which are able to be inserted into a procaryotic or eukaryotic host organism and which comprise, respectively, a sequence of DNA coding at least a portion of the sequence between aa540 and aa601, inclusive, read in the direction from the aminic end to the carboxylic end, of the viral protein p130 of the HCMV virus, and a sequence of DNA coding at least a portion of the sequence between aa1144 and aa1233, inclusive, read in the direction from the aminic end to the carboxylic end, of the viral protein p130. Both of these plasmids have been deposited at the American Type Culture Collection (ATCC), in Rockville, Md., USA, on the date May 29, 1996, in accordance with the modalities which are provided by the Treaty of Budapest, and have received the access numbers ATCC 98 065 and 98 066, respectively.

In accordance with a further aspect of the invention, this also includes two other plasmids, which are both able to be inserted into a prokaryotic or eukaryotic host organism; both of these plasmids have been deposited at the ATCC, on the date Apr. 30, 1996, in accordance with the modalities which are provided by the Treaty of Budapest, and are referred to as pCMV-1A (ATCC access number 98 042) and as pCMV-5A (ATCC access number 98 044), respectively. These two plasmids can produce the immunogenic sequences A1C2F3 of the protein pp150 and the sequence H10 of the protein pp52 fused with the CKS. These sequences have been noted in the PCT patent application, number WO 96/01321, the contents of which are hereby incorporated in their entirety, for reference. The invention also includes a recombinant host organism comprising the plasmids pCMV-1A or pCMV-5A.

Finally, the invention includes recombinant protein materials which are able to bond with the antibodies specific for HCMV and which consist of recombinant proteins expressed in a host organism into which one of the plasmids pCMV-30, pCMV-31, pCMV-1 A or pCMV-5A has been inserted. In particular, the present invention includes the proteins:

$$CKS_{(1-171aa)}\text{-}p130_{(540-601aa)}\text{-T-R-}CKS_{(171-260aa)}; \quad [2]$$

$$CKS_{(1-171aa)}\text{-}p130_{(1144-1233aa)}\text{-T-R-}CKS_{(171-260aa)}; \quad [3]$$

in which $CKS_{(1-171aa)}$ and $T\text{-}R\text{-}CKS_{(171-260aa)}$ represent, respectively, the residues of the CKS protein of aa1 to aa171, inclusive, read in the direction from the aminic end to the carboxylic end, and of the aa171 to aa260, inclusive, read in the direction from the aminic end to the carboxylic end; T and R are threonine and arginine, respectively; $p130_{(540-601aa)}$ represents the residue of the viral protein p130 from aa540 to aa601, inclusive, read in the direction from the aminic end to the carboxylic end; and, $p130_{(1144-1233aa)}$ represents the residue of the said viral protein p130 from aa1144 to aa1233, inclusive, read in the direction from the aminic end to the carboxylic end.

There are also covered by the present invention the diagnostic reagents for the serological diagnosis of the HCMV and derivatives of the recombinant protein materials described above and any diagnostic kit for the identification, by means of the serological method, of the presence of anti-HCMV antibodies comprising such diagnostic reagents.

BRIEF DESCRIPTION OF THE DRAWINGS

FIG. 3 contains Table 1, which presents the reactivity of the IgM observed between 500 samples of serum from blood donors;

FIGS. 4-A and 4-B contain Table 2 (which begins in FIG. 4-A and continues in FIG. 4-B), which summarizes the temporal development ("follow up") of sera withdrawn from the receivers of transplanted organs;

FIG. 5 contains Table 3, which presents the reactivity to the Combo WB test of selected human sera;

FIG. 6 depicts experimental strips in accordance with the test of the invention; the numbers on the left-hand side of the figure indicate apparent molecular weights of polypeptides under denaturing conditions (vp=viral protein; rp=recombinant protein; $\mu=\mu$ chain purified of the human immunoglobulins of class M); the numbers at the top of the figure refer to different samples of serum: 1–3. Pregnant women—IgG/IgM—positive (EIA); 4 and 5. Recipients of renal transplant IgG/IgM—positive (EIA); 6 and 7—Pregnant women IgG—positive, IgM—negative (EIA);

FIG. 8 is a schematic representation of a diagnostic tool in accordance with the invention for the identification of specific anti-HCMV IgM.

With reference to FIG. 8, there is indicated by (1) a diagnostic tool for the identification of specific anti-HCMV IgM in the human serum, comprising a means of solid support (2), such as a strip of nitrocellulose, for example, which bears a plurality of bands, each of which is formed from one or more proteins positioned in accordance with a predetermined pattern. In particular, the support strip (2) comprises two sections (3) and (4); the first section (3) bears a first series (5-a) (5-b) (5-c) (5-d) (5-e) formed by the viral proteins and spaced from one another at the intervals ($i_1$), ($i_2$), ($i_3$), ($i_4$); the second section (4) bears a second series of bands ($6_a$), ($6_b$), ($6_c$), formed by recombinant proteins and spaced one from one another by the intervals ($e_1$), ($e_2$); the second section (4) comprises, in addition, two control bands (7) and (8). The bands (5-a) (5-b) (5-c) (5-d) (5-e) are formed, preferably, by the viral proteins of HCMV vp28, vp38, vp65, vp82 and vp150, respectively, obtained from the virions purified by means of electrophoretic fractioning on polyacrylamide gel and absorbed on the support strip (2): the bands (5-a) (5-b) (5-c) (5-d) (5-e) are therefore positioned in accordance with the typical electrophoretic pattern, and the distances ($i_1$), ($i_2$), ($i_3$), ($i_4$) are proportional among themselves to the differences between the respective molecular weights. Obviously, the viral proteins could be obtained and transferred to the support in a different manner, in which case the distances ($i_1$), ($i_2$), ($i_3$), ($i_4$) would be different and the bands would be positioned in accordance with another pattern. The bands ($6_a$), ($6_b$), ($6_c$) are formed by the recombinant proteins which are obtained, for example, by means of the techniques of genetic engineering, incorporating into the exogenous protein CKS one or more immunogenic regions of the viral proteins p130, pp52 or pp150, respectively. The first control band (7) is formed from the protein CKS by itself, while the second control band (8) includes aliquots of heavy $\mu$ chains of human immunoglobulin.

Figure 1:
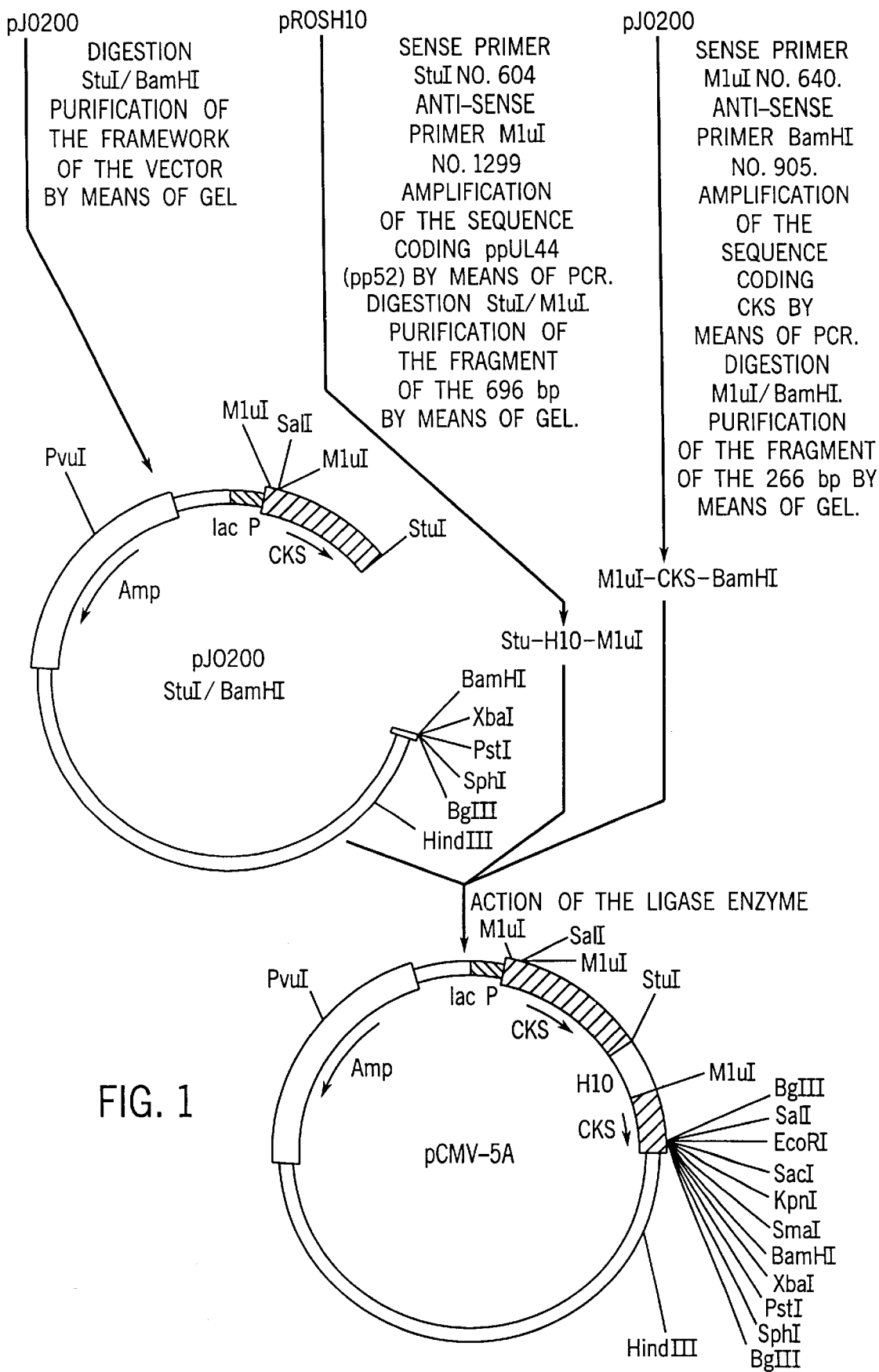
FIG. 1 is a schematic representation of the construction of the plasmid pCMV-5A.

During use, each band of both the sections (3) and (4) is tested with the serum which is under examination and with a developing substance: after the incubation of the proteins which form the bands with the serum, the appearance of a blot corresponding to one band reveals a reaction between the protein of that band and the IgM and, as the result, the presence of the said antibodies in the serum which is being examined. A cross-checking between the responses of the two sections (3) and (4) makes it possible to avoid possible non-specific results, as could happen with the traditional WB tests. In addition, the two control bands (7) and (8) make it possible to recognize results which are falsely positive or negative: a reaction in band (7), which is formed by the protein CKS, indicates, in fact, the presence of anti-CKS antibody in the serum, and the test will probably give a result which is falsely positive; if, on the other hand, the band (8), including the chain $\mu$, does not react, then an error in the execution of the test has probably been verified, and the result will be a false negative.

At the basis of the invention, as will be better described in the following, the test is only considered to be positive when at least one viral protein in the first section (3), and at least one recombinant protein in the second section (4), react simultaneously with the serum which is under examination, while the exogenous protein which constitutes the first control band (7) does not react, and the heavy chain of human immunoglobulin which forms the second control band (8) does react.

The test is considered to be doubtful if one or more bands of the recombinant section (4) turn out to be reactive but, within section (3), only the band which is formed by the viral protein vp82 reacts.

Finally, the test must be repeated if the control band (8) does not react since, in the said case, an error in the execution of the test is probably verified (the $\mu$ chain of human immunoglobulin must always react).

The present invention will now be further described, for the purpose of its better comprehension, in the following non-limitative examples.

EXAMPLE 1

General Methodology

1. Materials and Sources

The restriction enzymes, the ligases of the phage T4, the alkaline phosphatases of calf intestine (CIAP), the kinase polynucleotide, and the Klenow fragment of the polymerase I DNA were acquired from New England Biolabs, Inc. (Beverley, Mass. USA), or else from Boehringer Mannheim Corp. (Indianapolis). The DNase I and the aprotinine were acquired from Boehringer Mannheim Corp.

The standard molecular weights, both for DNA as well as for the proteins, the preformed acrylamide gel from Daiichi, and the system semi-dry transfer, along with the corresponding buffers, were acquired from Integrated Separation Systems, Inc. (Natick, Mass., USA).

The isopropyl-β-thiogalactoside (IPTG), acrylamide, N'N'-methylene-bis-acrylamide, N,N,N'N'-tetramethylethylenediamine (TEMED), 4-chloro, 1-naphtholo, the colorant Coomassie Blue™, and the sodium dodecyl sulfate (SDS) were acquired from Bio Read Laboratories (Richmond, Calif. USA).

The antibodies marked with peroxidase from raphania (HRPO) were acquired from Kirkegaard & Perry Laboratories, Inc. (Gaithersburg, Md., USA). The cells of coli Epicurean Coli™ XL-1 Blue (recA1 endA1 gyrA96 thi-1 hsdR17 supE44 relE44 relA1 lac [F' proAB lacIq ZΔ15 Tn (Tet')], the DNA purification kit, the RNA purification kit, as well as the kit for the synthesis of cDNA ZAP™, were acquired from Stratagene Cloning Systems, Inc. (La Jolla, Calif., USA).

The GeneAmp™ reagents kit and the DNA polymerase AmpliTaq™ were acquired from Perkin-Elmer Cetus (Norwalk, Conn., USA). The triphosphate deoxynucleotides which were used in the general procedures were taken from the GeneAmp™ kit.

The membrane of nitrocellulose with the support was acquired from Schleicher & Schüll (Keene, N.H., USA).

The kit of nucleotides for the sequencing of the DNA with Sequenase™ and 7-deaza-dGTP and the DNA polymerase Sequenase™, Version 2.0, were acquired from the U.S. Biochemical Corp. (Cleveland, Ohio, USA).

The kit for the purification of the mRNA poliA$^+$ was acquired from Pharmacia LKB Biotechnology, Inc. (Piscataway, N.J., USA).

The plates of Luria broth containing ampicillin (LBamp plates) were acquired from Micro Diagnostics, Inc. (Lombard, Ill., USA).

The medium OPTI-MEM, the fetal bovine serum, the saline phosphate buffer, the suitable cells of $E.$ $coli$ DH5a (Ø-F80dlacZDM15 D(lacZYA-argF)U169 deoR recA1 endA1 phoA hsdR17(rK, mK$^+$) supE44 1$^-$ thi-1 gyrA96 relA1), and the agarose gel ultraPURE™ were acquired from GIBCO BRL, Inc. (Grand Island, N.Y., USA).

The Bacto-Tryptone, the Bacto Yeast extract, as well as the Bacto-Agar were acquired from Difco Laboratories (Detroit, Mich., USA).

The NZY™ broth was purchased from Becton Dickinson Microbiology Systems (Cockeysville, Md., USA).

The DNA from salmon sperm, as well as the lysozyme, ampicillin, N-lauroylsarcosin, timerosal, buffers, hydroxylate acid of casein, the TWEEN 20™ (polyoxyethylene sorbitan monolaurate), diethylpyrocarbonate (DEPC), phenylmethylsulfonofluoride (PMSF), the bovine seroalbumine (BSA), urea, glycerol, EDTA, sodium deoxycholate, and inorganic salts were acquired from Sigma Chemical Co. (Saint Louis, Mo., USA).

The hydrogen peroxide ($H_2O_2$) was acquired from Mallinkrodt (Paris, Ky., USA), and the methanol was acquired from EM Science (G[i]bbstown, N.J., USA).

2. Mediums, Buffers and Generic Reagents

The "SUPERBROTH II" contains 11.25 g/l of tryptone, 22.5 g/l of extract of yeast, 11.4 g/l potassium phosphate dibasic, 1.7 g/l of potassium phosphate monobasic and 10 ml/l of glycerol, with a pH adjusted to 7.2 by means of sodium hydroxide.

The "Tri saline buffer", or "TBS", consists of 20 mM Tris, 500 mM NaCl at pH 7.5. The "TWEEN 20™ Tris saline buffer", or "TBST", consists of TBS plus 0.05% of TWEEN 20™.

The "membrane blocking solution" consists of bovine seroalbumine (BSA) at 1%, acid hydrolysate of casein at 1%, and 0.05% of TWEEN 20™ in TBS.

The buffer "Dilution rubazyme of the sample", or "Rubazyme SDB", is composed of Tris 100 mM at pH 7.5, NaCl 135 mM, EDTA 10 mM, TWEEN 20™ at 0.2%, timerosal at 0.01%, and fetal bovine serum at 4%.

The buffer "Dilution rubazyme of the conjugate" is composed of Tris 100 mM at pH 7.5 with NaCl 135 mM, Timerosal at 0.01%, and fetal bovine serum at 10%.

The "HRPO color development solution" is constituted by 4-chloro-1-naphtholo at 0.06%, $H_2O_2$ at 0.02%, and methanol at 0.2% in TBS.

The "SDS-PAGE loading buffer" is formed from Tris 62 mM at pH 6.8 with SDS at 2%, glycerol at 10%, β-mercaptoethanol at 5%, and blue of bromophenol at 0.1%.

The "TE buffer" is constituted by Tris 10 mM and EDTA 1 mM at pH 8.0.

The "buffer of TEM lysis" is constituted by 50 mM Tris, 10 mM EDTA, and $MgCl_2$ 20 mM at pH 8.5.

The "PTE buffer" is constituted by Tris 50 mM and EDTA 10 mM, at pH 8.5.

3. Propagation of the virus and preparation of the cDNA

The strains AD169 or Towne of the HCMV virus, cultivated in human fibroblasts grown in the medium OPTI-MEM™ containing fetal bovine serum at 5%, are used without distinction. The strain HCMV AD 169 and the genome of HCMV are described in the publications by Chee et al., *Curr. Top. Microbiol. Immuno.*, 154:125 (1990) and Bankier et al., *DNA Seq.* 2:1 (1991), with this information being incorporated into the present text by way of reference.

Six (6) days after the infection of fibroblasts infected with HCMV, these were collected and centrifuged, washed with PBS and homogenized with a vetro-Teflon™ homogenizer. The total viral DNA was isolated as described by Mocarski et al., in *Proc. Nat'l. Acad. Sci.*, 82:1266 (1985). The total RNA was isolated from the homogenized cells using the purification kit of the RNA (Stratagene Cloning Systems), and the RNA polyA$^+$ was isolated by means of a purification kit of the RNA messengers (Pharmacia Biotech). The cDNA of HCMV was synthesized from viral mRNA purified by means of a ZAP-cDNA™ synthesis kit.

4. General Methods

All of the enzymatic digestions of the DNA have been carried out in accordance with the instructions of the manufacturers. At least 5 units of enzyme were used per microgram of DNA, and the reactions were allowed to proceed for incubation times which were sufficient for the complete digestion of the DNA. The protocols which were supplied by the manufacturers were followed for the use of the various DNA and RNA manipulation kits, for the synthesis of DNA with the polymer chain reaction (PCR), and for the sequencing of the DNA. Standard procedures were followed for the preparation, on a mini scale or on a large scale, of plasmidic DNA of *E. coli,* for the preparation of DNA from phagic lysates from the cells of *E. coli* infected with λ phage, for the preparation of lysates of *E. coli* for the adsorption of anti-*E. coli* antibodies, for the extraction with phenol-chloroform and the precipitation of the DNA, for the analyses of the restriction on agarose gel, for the purification of DNA fragments of the gel of agarose and polyacrylamide, for the filling of the incomplete 3' end (carboxylic end) of the DNA, created by means of digestion with restriction enzymes, by means of the Klenow fragment of the polymerase I DNA, by means of the ligation of fragments of DNA with the ligase of the T4 phage, and for the preparation of the suitable TB1 cells (Fara d(lac-proAB) rpsl Ø-80dlacZDM15 bsdR17) (Maniatis. et al., in *Molecular Cloning: A Laboratory Manual,* 2nd ed., Cold Spring Harbor Laboratory Press, New York, 1989).

The fragments of DNA for the cloning in plasmids generated by means of amplification with PCR were extracted with phenol-chloroform and precipitated with ethanol before this was digested with the restriction enzymes. The oligonucleotides which were used in the PCR and in the sequencing of the DNA were synthesized in an oligonucleotides synthesizer from the firm Applied Biosystems, Model 380 B or 394, following the protocols of the manufacturer.

5. Construction of the Vectors

The construction of the precursor plasmids pJO200, pEE1, pMB34, and pROSHI10 has been described in the international patent application which was published under the number WO 96/01321, and in the article by Landini et al. [4].

EXAMPLE 2

Construction of pCMV-1A: CKS-A1C2F3-CKS

The plasmid pCMV-1A, which is derived from the plasmid pJO200, was constructed by cloning a fragment of DNA containing HCMV-A1C2F3 which was obtained, in its turn, by means of PCR amplification of the DNA A1C2F3 which is contained in pMB34, at the site StuI of pJO200, as described in the international patent application which was published under the number WO 96/01321, and in the article by Landini et al. [4]. The plasmid pCMV-1A was filed with the ATCC on the date Apr. 30, 1996, in accordance with the modalities which are provided by the Treaty of Budapest, and has been given the ATCC Access Number ATCC 98 042.

EXAMPLE 3

Construction of pCMV-5A: CKS-H10-CKS

The plasmid pCMV-5A, a derivative of the plasmid pJO200 (FIG. 1), was constructed by cloning a fragment of DNA containing HCMV-H10, which was obtained, in its turn, by means of PCR amplification of the DNA H10 which is contained in pROSH10, in the site StuI of pJO200. The plasmid pCMV-5A was filed with the ATCC, on the date Apr. 30, 1996, in accordance with the modalities which are provided by the Treaty of Budapest, and has been given the ATCC Access Number ATCC 98 044.

The purification of the plasmidic DNA (pROSH10 and pJO200) on a vast scale has been carried out by means of general methods. The DNA of the plasmid pJO200 was digested with StuI and BamHI, and the framework of the purified vector on agarose gel. The StuI/BamHI digestion eliminated a portion of the 3' end of the CKS gene, which was reconstituted following the "ligation" reaction. Two fragments of DNA obtained by PCR amplification have been cloned in this framework of the vector in a three-way "ligation" reaction. H10 was cloned as the DNA fragment StuI/MluI, and the remaining portion 3' of the gene CKS was cloned as the MluI/BamHI fragment of DNA, thus reconstituting the complete CKS gene.

There were synthesized a sense primer, which arises from the nucleotide 604 of ppUL44 and contains an StuI site, and an anti-sense primer, which arises from the nucleotide 1299 of ppUL44 and contains an MluI site, and these were added to the mixture of the PCR reaction which contains the plasmid pROSH10. Following the amplification by means of the PCR, the reaction mixture was digested with StuI and MluI, and the DNA fragment of 696 pb which results, and which contains H10, was purified on agarose gel. There have been synthesized a sense primer, which arises from the nucleotide 640 of pJO200 (containing the MluI site) and an anti-sense primer, which arises from the nucleotide 905 of pJO200, and added to the mixture of PCR reaction containing the plasmid pJO200 (the nucleotidic numberings which were previously stated correspond to the sequence of DNA which is shown in FIG. 12 as pJO200 in the international patent which was published, under the number WO 96/01321, by Landini et al.). After the amplification by means of PCR, the reaction mixture was digested with MluI and BamHI, and the DNA fragment of 266 pb which resulted, and which contained the 3' portion of the CKS gene, was purified by means of gel. These fragments of purified DNA which were obtained were subsequently ligated to pJO200/StuI/BamHI overnight at 16° C. On the next day, the mixture of ligation was introduced, for the purpose of transformation, into suitable cells of XL-1 Blue.

DNA was then prepared on a mini scale by means of transformation agents and analyzed for the presence of H10 inserted at the StuI site of pJO200. The plasmid pCMV-5A has turned out to contain H10 inserted into the site StuI. The sequences of DNA of H10, and the 3' end of CKS, have been confirmed by means of DNA sequencing. The coding region of the CKS-H10-CKS construct which codes the protein rpCMV-5A has turned out to contain a bridge of two amino acids (threonine and arginine) conferred with the MluI site between H10 and the 3' end of CKS. In addition, the amino acid 171 of CKS has been duplicated in the construct, which has been designated as follows:

$$CKS_{(1-171aa)}\text{-H10-T-R-}CKS_{(171-260aa)}; \quad [1]$$

in which T and R are the residues of threonine and arginine, respectively, coded from the synthesis sites PstI and MluI introduced into the vector.

EXAMPLE 4

Construction of the Vectors Based on pEE1 Expressing CKS-pUL57-CKS

The vector pEE1 which expresses the protein CKS has been used as the starting plasmid for the construction of two CKS-pUL57-CKS fusion constructs. For each construct, the plasmid pEE1 has been digested with StuI and MluI and the framework of the purified vector. The structure pEE1/StuI/MluI has been able to accept fragments of the gene pUL57, generated by means of the PCR amplification, which had an StuI site at the 5' end (aminic end) and an MluI site at the 3' end (carboxylic end). After the digestion with StuI and MluI, the fragments of the gene pUL57 were cloned 'in frame', by means of PCR, in the framework pEE1/StuI/MluI. The fusion proteins CKS-pUL57-CKS which are expressed by these vectors have been designated in the following manner:

$$CKS_{(1-171aa)}\text{-pUL57-T-R-}CKS_{(171-260aa)};$$

in which T and R are the residues of threonine and arginine, respectively, coded at the PstI and MluI synthesis sites introduced into the vector.

Phase 1: Construction of pCMV-30: $CKS\text{-pUL57}_{(540-601aa)}\text{-}CKS$

Figure 2A:
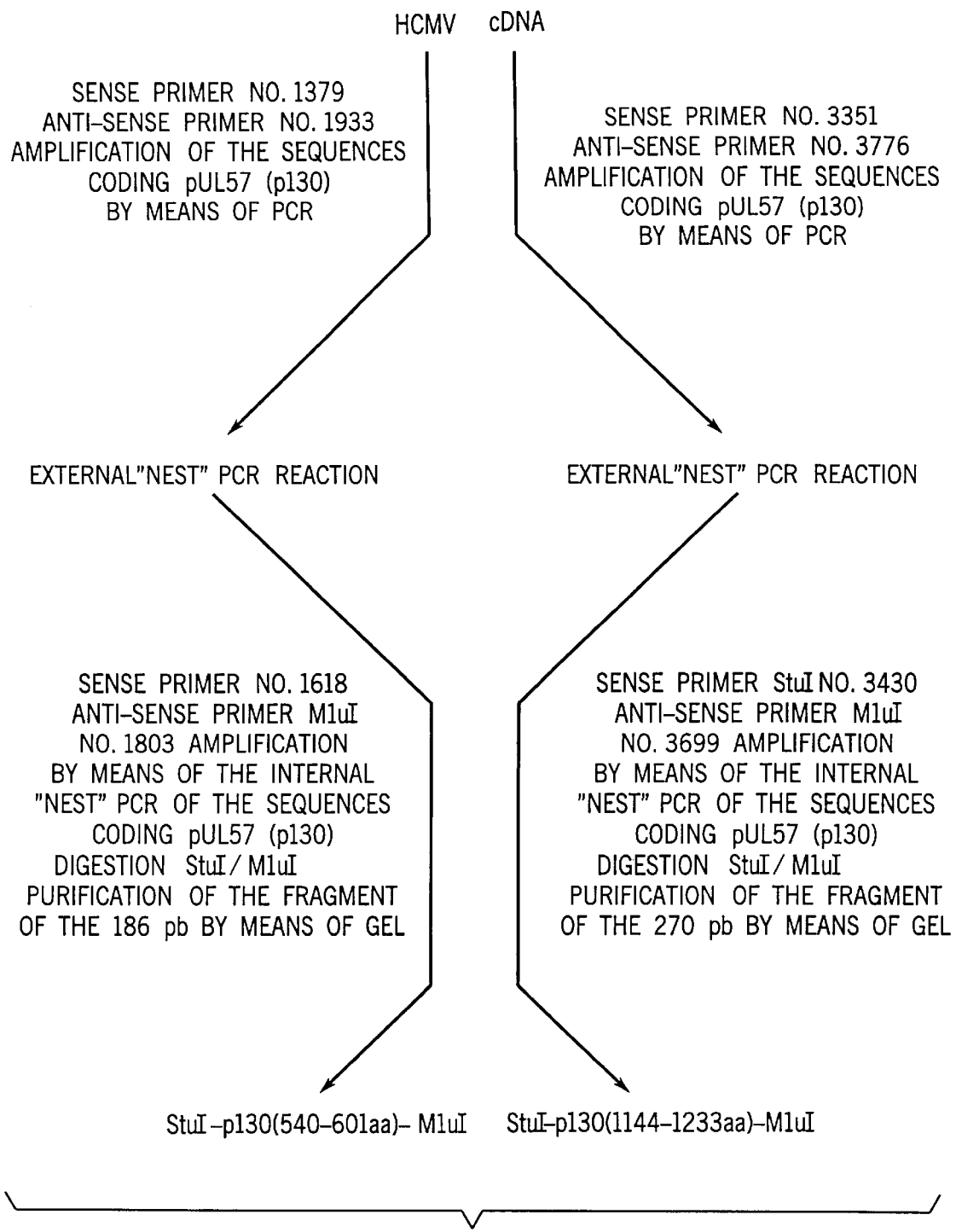
FIG. 2 is a schematic representation of: (A) preparation of the PCR fragments containing the sequences of DNA p130 $_{(540-601aa)}$ and p130$_{(1144-1233aa)}$; (B) construction of the plasmids pCMV-30 and pCMV-31.
Figure 2B:
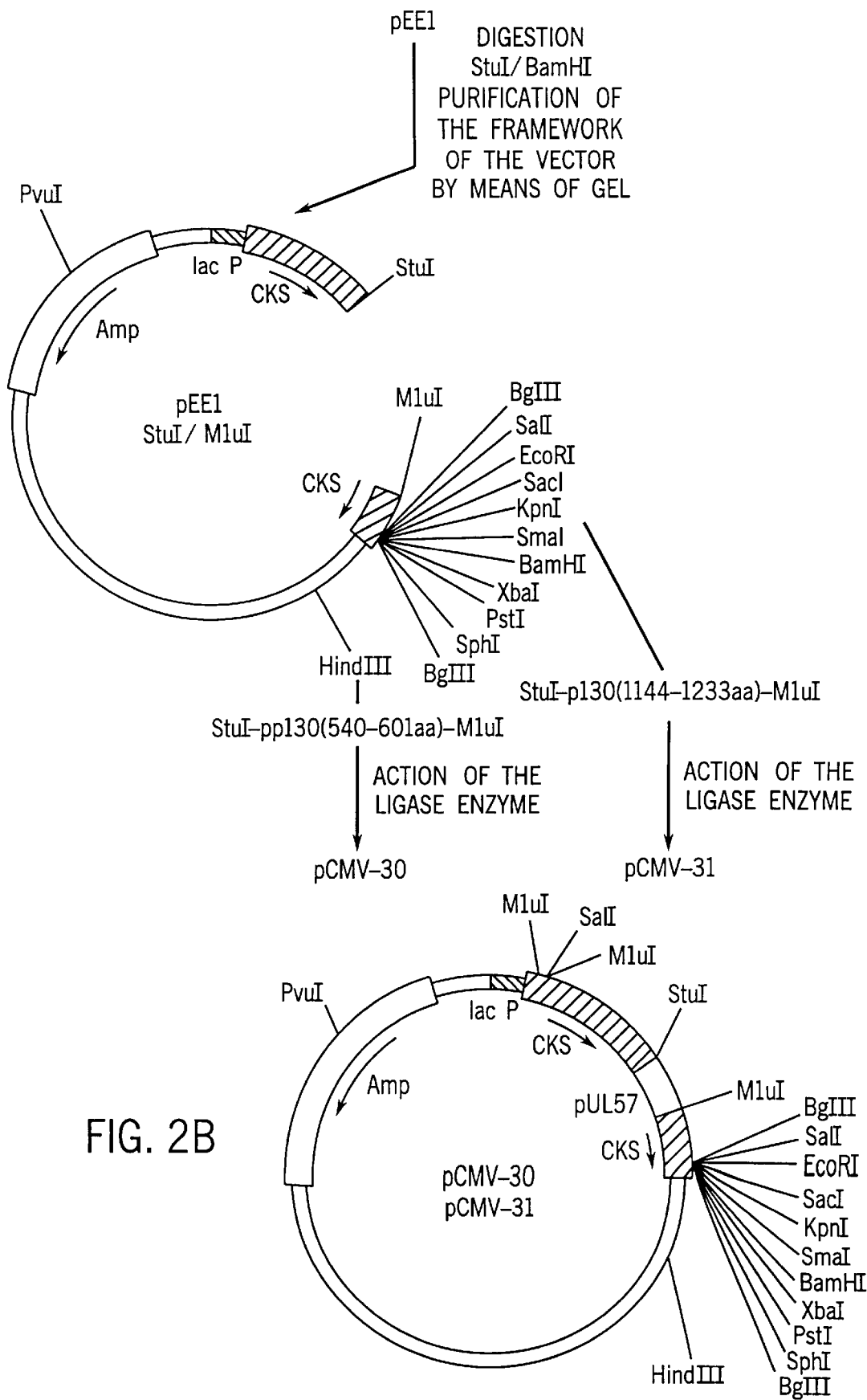

The plasmid pCMV-30, a derivative of the plasmid pEE1 (FIGS. 2-A and 2-B), has been constructed by cloning a fragment of DNA containing $HCMV\text{-}p130_{(540-601aa)}$, obtained by amplification with PCR of cDNA of HCMV of the region of pUL57 which codes the amino acids 540–601 into pEE1. The fragment of DNA which is used is constituted by the 1618–1803 nucleotides of pUL57, where the nucleotides 1 and 3776 correspond to the nucleotides 90281 and 86506, respectively, of the supplemental filament of the published sequence of AD169. The plasmid pCMV-30 has been filed with the ATCC in accordance with the modalities which are provided by the Treaty of Budapest, and has been assigned the Access Number ATCC 98 065.

Using the cDNA of HCMV as a template, the DNA fragment $HCMV\text{-}p130_{(540-601aa)}$ has been produced in two phases ('nested') by means of an amplification reaction with PCR. For the external nested amplification reaction, there have been synthesized a sense primer which arises from the nucleotide 1379 and pUL57, and an anti-sense primer which arises from the nucleotide 1933 of pUL57: both were subsequently added to the mixture containing the cDNA. After the amplification with PCR, the mixture of the external nested amplification has been used as a template for the internal nested PCR amplification reaction. For the internal reaction, there have been synthesized a sense primer which arises from the nucleotide 1618 of pUL57, which contains an StuI site, and an anti-sense primer which arises from the nucleotide 1803 of pUL57, which contains a PstI site: both were then added to the mixture containing amplified DNA in the external nested reaction. Following the amplification reaction with PCR, the reaction mixture was digested with StuI and PstI, and the fragment of 186 pb which contains $p130_{(540-601aa)}$ has been purified on the agarose gel.

The plasmidic DNA (pEE1) has been produced on a large scale by means of generic methods. The plasmid pEE1 has been digested with StuI and MluI, and the framework of the vector pEE1/StuI/MluI has been purified on agarose gel. The DNA fragment HCMV-$p130_{(540-601aa)}$ StuI/PstI, purified, was ligated to the vector pEE1/StuI/MluI overnight at 16° C. On the next day, the ligation mixture was inserted, by means of transformation agents, into suitable XL-1 Blue cells. The transformation agent was prepared, on a mini scale, from the plasmidic DNA, which was subsequently analyzed for the presence of DNA fragments HCMV-$p130_{(540-601aa)}$ inserted into the StuI/MluI sites of pEE1: the plasmid pCMV-30 turned out to effectively contain $p130_{(540-601aa)}$ located on the StuI/MluI sites of pEE1. The DNA sequence of $p130_{(540-601aa)}$ was additionally confirmed by means of the sequencing of the DNA. This fusion construct, CKS-CMV-CKS, has been designated as follows:

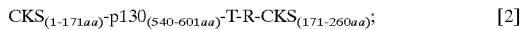

$$CKS_{(1-171aa)}\text{-}p130_{(540-601aa)}\text{-}T\text{-}R\text{-}CKS_{(171-260aa)}; \qquad [2]$$

in which T and R are the residues of threonine and arginine, respectively, coded from the synthesis sites PstI and MluI introduced into the vector.

Phase 2: Construction of pCMV-31: CKS-$pUL57_{(1144-1233aa)}$-CKS

The plasmid pCMV-31, a derivative of the plasmid pEE1 (FIGS. 2-A and 2-B), was constructed by cloning a fragment of DNA containing HCMV-$p130_{(1144-1233aa)}$, which was obtained by amplification, by means of PCR, from the cDNA of HCMV of the region of pUL57, which codes the amino acids 1144–1233 into pEE1. The fragment of DNA which was used is constituted by the nucleotides 3430–3699 of pUL57, where the nucleotides 1 and 3776 correspond to the nucleotides 90281 and 86506, respectively, of the supplementary filament of the published sequence of AD 169. The plasmid pCMV-31 has been filed with the ATCC in accordance with the modalities which are provided by the Treaty of Budapest, and has been assigned the Access Number ATCC 98 066.

Using cDNA of HCMV as a template, the DNA fragment HCMV-$p130_{(1144-1233aa)}$ has been produced by means of an amplification reaction, by means of PCR, in two phases ('nested'). For the external nested amplification reaction, there have been synthesized a sense primer which arises from the nucleotide 3351 of pUL57, as well as an anti-sense primer which arises from the nucleotide 3766 of pUL57: both have subsequently been added to the mixture containing the cDNA. After the amplification with PCR, the mixture of the external nested amplification has been used as a template for the internal nested PCR amplification reaction. There have been synthesized for the internal reaction a sense primer which arises from the nucleotide 3430 of pUL57, containing an StuI site, and an anti-sense primer which arises from the nucleotide 3699 of pUL57, which contains a PstI site: both have then been added to the mixture containing amplified DNA in the external nested reaction. Successive to the amplification reaction by means of the PCR, the reaction mixture has been digested with StuI and PstI, and the fragment of 270 pb containing $p130_{(1144-1233aa)}$ has been purified on agarose gel.

The plasmidic DNA (pEE1) has been produced on a large scale by means of generic methods. The plasmid pEE1 has been digested with StuI and MluI, and the framework of the vector pEE1/StuI/MluI has been purified on agarose gel. The DNA fragment HCMV-$p130_{(1144-1233aa)}$PstI/MluI, purified, were ligated to the vector pEE1/StuI/MluI overnight at 16° C. The next day, the ligation mixture was inserted, by means of transformation, into suitable XL-1 Blue cells. The plasmidic DNA was prepared from the transforming agents, on a mini scale, and was thereupon analyzed for the presence of the DNA fragments HCMV-$p130_{(1144-1233aa)}$ inserted into the StuI/MluI sites of pEE1: the plasmid pCMV-31 turned out to effectively contain $p130_{(1144-1233aa)}$ located on the StuI/MluI sites of pEE1. The DNA sequence of $p130_{(1144-1233aa)}$ was additionally confirmed by means of the sequencing of the DNA. This fusion construct, CKS-CMV-CKS, has been designated as follows:

$$CKS_{(1-171aa)}\text{-}p130_{(1144-1233aa)}\text{-}T\text{-}R\text{-}CKS_{(171-260aa)}; \qquad [3]$$

in which T and R are the residues of threonine and arginine, respectively, coded from the synthesis sites PstI and MluI introduced into the vector.

EXAMPLE 5

Production and Purification of Recombinant Antigens of HCMV

1. Expression of the Genes of HCMV

The bacterial control strain which expresses the protein CKS, not fused, and all of the bacterial clones expressing fusion proteins of HCMV, as in Example 2 [rpCMV-1A (A1C2F3/ppUL32/pp105)], from the Example 3 [rpCMV-5A(H10/ppUL44/pp52)], and from Example 4 [rpCMV-30 (pUL57/p130) and rpCMV-31(pUL57/p130], were cultivated in the medium "SUPERBROTH II", which contains 100 μg/ml of ampicillin up to the logarithmic phase of growth; the protein synthesis of the CKS-HCMV fusion was induced by means of the addition of IPTG as described in [9]. At 4 hours from the induction, the cells were collected by means of centrifuging and the pellets were frozen at −80° C. up to the moment of purifying the proteins.

2. Purification of the Non-fused CKS Protein and of the CKS-HMV Recombinent Proteins The insoluble CKS-HCMV fusion proteins (rpCMV-1A, rpCMV-5A, rpCMV-30, rpCMV-31) have been purified after lysis by means of a combination of washings with detergent, followed by solubilization in 8M urea [9]. The soluble CKS protein was purified after cellular lysis by means of precipitation with ammonium sulfate followed by DEAE chromatography.

EXAMPLE 6

Experimental Tests—"Combo WB"

1. Samples of Human Serum

Five hundred samples of serum from blood donors, which had been selected at random from a collection of sera, were tested in order to evaluate the level of specificity of the Combo WB in comparison with the traditional EIA, with particular attention being given to the false positives.

In order to valuate the sensitivity of the Combo WB test, 100 sera were selected from among the samples which had turned out to be positive to the anti-CMV IgM, as determined by means of different procedures, specifically, two commercial EIA tests and the traditional WB test. Only those samples which had turned out positive in all three of the tests were inserted into this group and were used thereafter. In order to further valuate the sensitivity of the test, another two groups of samples were selected: 85 sera withdrawn from recipients of heart transplant (HTR), with one PCR positive for HCMV in polymorphonucleoleukocytes (PMNL), and 38 sera from women in pregnancy with infection from HCMV, as demonstrated by means of the isolation of the virus from the urine, or by means of the seroconversion of the IgG.

In addition, for the purpose of determining the time of appearance and the development of the immune response to the HCMV virus as determined by the Combo WB test, a temporal investigation ("follow up") was carried out on 10 recipients of transplants, from whom a total of 74 blood samples were withdrawn, which samples were analyzed either for antigenemia or for the investigation of anti-CMV specific IgM with the conventional EIA and with the Combo WB.

2. Virological Diagnosis of the Infection on a Portion of the HCMV Virus 2.1 Isolation of the Virus The "shell vial" procedure [1] was used to isolate the virus from the urine and from the saliva. The human fibroblastoid cells which were inoculated with the pathological material were fixed 24 to 48 hours after the inoculation, and colored by means of indirect immunofluorescence (IIF), using a monoclonal antibody which reacts with the genic product HCMV-IE1/IE2(E13 from the firm Bioline, Paris, France).

2.2 Antigenemia

The presence of HCMV-pp65 in a PBL fraction enriched in PMNL was determined in the manner which was originally described by Van der Biji et al. [10] and modified by Revello et al. [8], by using a monoclonal HCMV-pp65 specific antibody (clone 1C3 from Argene, Paris, France) in indirect IIF tests.

The results were quantified under fluorescence microscopy, counting the number of cells out of 200,000 which were positive to pp65. One positive cell out of 200,000 was sufficient to define a result as being positive for antigenemia.

3. Serological Diagnosis of Infections from the HCMV Virus 3.1 Conventional EIA Tests The titration of the specific IgG's against the HCMV virus was carried out by using the Enzygnost alpha method EIA anti-CMV/IgG kit (Behring AG, of Marburg, Germany), which is available on the commercial market. The microplates were read by means of an automatic micro-reader for EIA (Behring AG). The valuation of the anti-CMV IgM was carried out by using an Enzygnost anti-CMV/IgM kit (from Behring AG). The results have been interpreted in accordance with the instructions which were provided by the manufacturers.

3.2 "Combo WB" Test for the Identification of Anti-CMV IgM

Using the traditional WB technique, as has already been described [3], lysates of purified virion were fractioned on polyacrylamide gel: the polypeptides which were thus separated were subsequently transferred to sheets of nitrocellulose, in accordance with their electrophoretic profiles. The sheets of nitrocellulose exceeded the length dimension of the gels by approximately one quarter, in such a manner as to leave sufficient space at their base for the recombinant proteins. After the electrophoretic transfer of the viral proteins, every blot was mounted on a mini-blotter in such a manner that the channels of the mini-blotter turned out to be oriented perpendicularly to the direction of migration of the proteins on the polyacrylamide gel; suspensions of the three recombinant proteins were deposited in the small well. In order to check the non-specific reactions against the protein vector and the correct identification of the immune complex, two control channels—in which a suspension of the CKS protein-vector and one of the $\mu$ chain of human immunoglobulin were deposited, respectively—were included. The mini-blotters were then held in light agitation on an oscillating platform for one night at 4° C. The filters were washed briefly in TBS, then saturated for incubation with a blocking solution (3% gelatin by fish, 1% BSA, 5% skim milk in powder, 0.05% Tween 20 in TBS) at ambient temperature for one hour. The filters were thereupon cut into strips of three millimeters in width, with each containing either authentic viral proteins (in the upper part) or recombinant polypeptides (in the lower portion), and were then constituted by means of a combination of a traditional WB section and of a section of recombinant bands. The strips of nitrocellulose which were described above have been used in serological analyses for the search for IgM's specific for HCMV in the human serum. The sera were diluted at the ratio of 1:50 in TBS in the presence of 4% fetal bovine serum (SBF), 0.1% Tween 20. The human anti-$\mu$ chain antibodies, conjugated with peroxidases anti-human IgM from goat), were diluted in TBS containing 10% of SBF.

3.3 Algorithm for the Interpretation of the Combo WB Test for Identification of IgM The WB section of the strip with the viral proteins is only considered to be positive when one of the following proteins has been found to be reactive against the human serum: pp150, pp65, p55, p38, p28. The recombinant section of the strip has been considered positive when at least one of the bands corresponding to the recombinant viral proteins was found to be reactive. The test has been considered:

Positive, when at least one reactive band of the traditional WB section of the strip has been confirmed by the reactivity of at least one band of the recombinant section;

Negative, if one of the two sections of the strip has been completely negative, independently of just how many bands turned out to be reactive in the other section;

Indeterminate or equivocal, if the sole positivity of the p82 in the WB section of the strip has corresponded to the positivity of one or more bands of the recombinant section.

A positive reaction in the position of the $\mu$ chain, and no reaction in the position of the protein-vector, were necessary in order to confirm the validity of the test.

3.4 Combo WB for the Identification of Anti-HCMV IgG or IgA

Combo WB strips, prepared as described above, can also be used in serological tests for the search in the human serum for IgG and IgA specific against the HCMV virus. The sera are diluted at the ratio of 1:100 in TBS in the presence of 4% of SBF and of 0.1% of Tween 20. The specific antibodies for the $\gamma$ and $\alpha$ chain, respectively, conjugated with peroxidase (anti-human goat IgM), are diluted in TBS containing 10% of SBF.

4. Results 4.4 Identification of IgM Specific Anti-HCMV with the Combo WB Test

Figure 7:
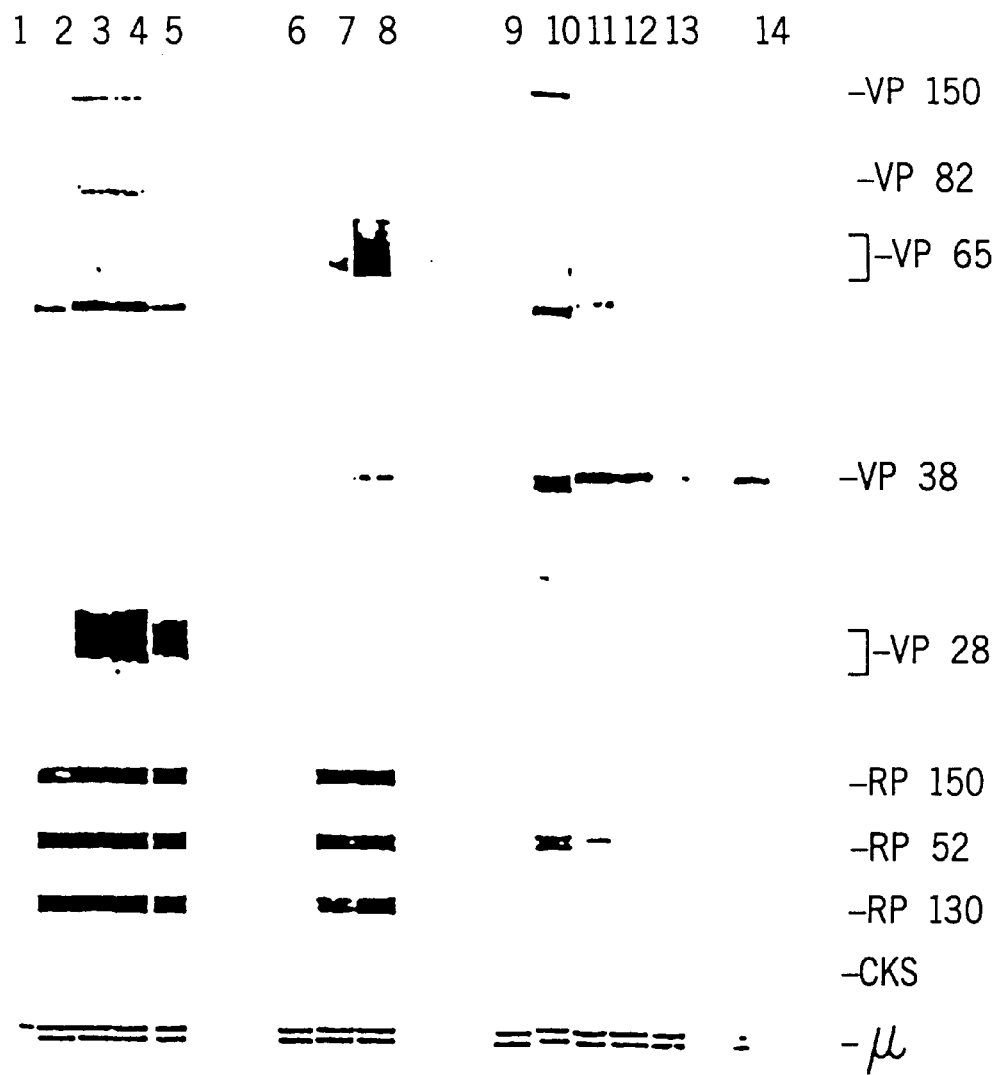
FIG. 7 is similar to FIG. 6 and shows: temporal development ("follow up") of pregnant women with primary infection (the virus has been transmitted to the fetus): 1. The first sample of serum withdrawn, negative (neg.) versus the IgG and the IgM; 2. Second sample, IgG neg, IgM positive (pos.); from 3 to 5. Successive samples withdrawn at intervals of two weeks, IgG and IgM pos.; 6. First sample, IgG and IgM neg.; 7. Second sample, IgG neg., IgM pos.; 8. Third sample, IgG and IgM pos.; 9. First sample, IgG and IgM neg.; 10–13. Successive samples withdrawn on a period of 7 months, IgG and IgM pos.; neonates with viruria: 14. Samples of IgG pos. serum, IgM neg.

In order to verify the specificity of the Combo WB test against the IgM's specific to HCMV, an increased number of samples coming from donors of blood and healthy individuals were examined in parallel to a traditional EIA test. A total of 500 sera were analyzed, 300 of which were collected in the United States and 200 in Italy. Some 79% of the sera were found to be positive for the IgG: 0.2% samples of serum were found to be positive against IgM from the traditional EIA test, and 1.8% by means of the combined method. The details of this analysis are summarized in Table 1: 14 sera (2.8%) reacted with the single vp150; 3 sera (0.6%) reacted with the single vp82; and a few other sera (not more than 0.4%) reacted only with one or more other viral proteins, but none of these has given reactions with the recombinant proteins; three sera (0.6%) reacted only with one or more recombinant proteins, without providing a concomitant reaction with any viral protein: both of these two groups of sera have been considered to be negative to the IgM. Nine sera (1.8%) reacted with at least one viral protein and one recombinant, and were for that reason considered to be positive to the IgM. In addition, in order to determine the sensitivity against the IgM of the second test of the invention, another 100 sera, which had been found to be positive for the IgM specific for HCMV either in the commercial EIA tests or in the traditional WB test, were analyzed with the Combo WB: 100% of such sera were found to be positive with the Combo WB test as well. In order to further valuate the sensitivity of the test, two other groups of sera were tested. A first group consisting of 85 samples withdrawn from patients with heart transplants, who had been found to have a positive PCR for the HCMV virus in PMNL, was analyzed for the presence of IgM specific to HCMV, both by means of a commercial EIA kit and with Combo WB: 39 were found to be positive with the commercial kit, while 58 were found to be positive with the Combo WB (Table 3). Finally, 38 samples of sera which had been obtained from pregnant women were selected on the basis of the presence of an active infection at the time of the collection. When these samples were analyzed for the presence of anti-HCMV IgM with the EIA test and the Combo WB test, 22 were found to be positive by means of the first technique and 34 by means of the second one (see Table 3). Some examples of reactivity of the samples of serum with the Combo WB test are shown in FIGS. 6 and 7. The sera were withdrawn from women in pregnancy with acute infection (FIG. 6, lines from 1 to 3), with advanced infection (FIG. 6, lines 6 and 7), and with primary infection with documented transmission of the virus to the fetus (FIG. 7).

With the objective of stabilizing the time of the appearance and the development of the immune response of the IgM as determined by the Combo WB in the case of acute infection, a further group of ten recipients of organ transplants was included in the experimental analysis, and a temporal investigation ("follow up") was carried out on the samples of serum withdrawn from these (in total: 74): the first sample was withdrawn from each recipient before the surgical intervention, the successive ones were withdrawn periodically, with intervals of between 2 and 78 days, inclusive; the sera were thereupon subjected in parallel to a test of Antigenemia, to a commercial EIA test for the IgM, and to the Combo WB. As shown in Table 2, in four cases, the three methods have shown a comparable sensitivity, and all of the tests have been judged positive for the first time in the said sample (Arq, Fir, Fer and Bat). In two cases (Fio and Bos), the Antigenemia test has been the first to reveal the reaction of the infection, with 14 and 9 days in advance, respectively; in one case (Cup), the Combo WB was the first, with 19 days in advance relative to the Antigenemia; in one case (Sab), Antigenemia and Combo WB have preceded the EIA by one week. One example of the reactivity of these sera in the Combo WB test is illustrated in FIG. 6, lines 4 and 5.

If only the serological analysis of the anti-CMV IgM is taken into consideration, the Combo WB has preceded the EIA test in two cases (Sab, Cup); in two other cases, the contrary was verified (Fio and Cic) whereas, in the six remaining cases, EIA and Combo WB were found to be positive at the same time.

4.2 Identification of Anti-HCMV IgA with the Combo WB Test

A modified version of the Combo WB test is applicable to samples of human serum for the identification of the IgG and IgA which are specific for the HCMV. Essentially, the strips of nitrocellulose are prepared in the same manner as that used for the specific search for the IgM, except for the fact, however, that recombinant proteins expressing portions of gB (UL55) and p28 (UL99) are used for the recombinant protein expressing a portion of pUL57.

5. Discussion

A new serological test, which is based upon the WB technical memorandum, has been worked out: this new test uses either native viral proteins or recombinant immunogens as the antigenic material.

In order to carry out a diagnostic product which has either the distinct specificity of an authentic viral material or the reliability of an antigen produced by means of recombination, viral products originating from infected cells and recombinant antigens obtained with techniques of genetic engineering have, in fact, been combined. The objective of the present invention is, in fact, to provide an antigenic material for HCMV which is commercially available with an internal standard which is able to confirm the indeterminate results and, at the same time, to enrich the assortment of viral targets which are recognizable by specific antibodies with non-structural viral antigens. A further objective of the present invention is to integrate a definite mixture of recombinant antigens of HCMV with authentic structural viral products in such a manner as to guarantee an internal reference for the reactivity of the human serum, as opposed to the recombinant proteins. In actual point of fact, the basis for the interpretation of the results is a direct consequence of this reciprocal internal control which constitutes the test itself: the test is, therefore, only considered to be positive when positivity is present in at least a significant band of both parts of the test.

The experimental results have shown that the Combo WB test in accordance with the invention is:

1) More sensitive than the traditional EIA test (Behring);

2) More specific than the traditional WB test.

In point of fact, since it is documented that an average of between 0.3% and 1.1% of the samples of the serum withdrawn statistically in a population of blood donors or healthy adults are shown to be positive to the IgM of HCMV [7], the experimental results show that the Combo WB guarantees an increased specificity in relation to the traditional WB.

What is claimed is:

1. A diagnostic tool for the identification of anti-HCMV antibodies in the human serum, said diagnostic tool comprising a means of solid support, a first section of which bears a plurality of viral proteins (vp) which are obtained from the purified virions, with said viral proteins being concentrated in corresponding bands and the bands being supported by said first section of the solid support, spaced one from the other in accordance with a predetermined pattern; with one of said bands being formed by at least one viral protein of approximately 150 kD molecular weight; with said diagnostic tool comprising:

(i) Said means of solid support comprising, in addition, a second section containing a plurality of bands spaced among themselves in accordance with a predetermined pattern, with at least one first band of said second section including a single recombinant protein (rp) which comprises a first region reproducing a sequence of amino acids corresponding to at least one epitope of the viral protein pp150, and a second region reproducing at least a portion of the sequence of amino acids of an exogenous protein;

(ii) At least one second band of the second section including a recombinant protein which comprises a first region reproducing a sequence of amino acids corresponding to at least one immunogenic epitope of a first non-structural protein of the HCMV virus, and a second region reproducing said at least a portion of the sequence of amino acids of said exogenous protein; and:

(iii) At least one control band formed by said at least a portion of the sequence of amino acids of said exogenous protein, said at least a portion of the sequence of amino acids of said exogenous protein in (i) being identical to said at least a portion of the sequence of amino acids of said exogenous protein in (ii) and being further identical to said at least a portion of the sequence of amino acids of said exogenous protein in (iii).

2. A diagnostic tool in accordance with claim 1, wherein said recombinant protein which is included in said first band of the second section comprises said first region, which reproduces a sequence of amino acids (F3) corresponding to the sequence between aa1006 to aa1048, inclusive, read in the direction from the aminic end to the carboxylic end of the viral protein pp150; and, a third region, reproducing a sequence of amino acids (A1C2) corresponding to the sequence between aa595 and aa614, inclusive, read in the direction from the aminic end to the carboxylic end of said viral protein pp150; said regions capable of being positioned, one in relation to another, at different locations within said recombinant protein in said first band of said second section.

3. A diagnostic tool in accordance with claim 1, wherein said second band of the second section includes a recombinant protein, said first region of which reproduces a sequence of amino acids (H10) corresponding to the sequence between aa202 and aa434, inclusive, read in the direction from the aminic end to the carboxylic end of the viral protein pp52.

4. A diagnostic tool in accordance with claim 1, wherein said second section of said means for solid support supports at least a third band including at least one recombinant protein, which comprises a first region reproducing a sequence of amino acids corresponding to at least one epitope of a second protein of HCMV, structural or non-structural, and a second region reproducing at least a portion of the sequence of amino acids of the exogenous protein; said second viral protein, structural or non-structural, being selected in relation to the class of antibodies which are to be revealed by means of said diagnostic tool.

5. A diagnostic tool in accordance with claim 4, wherein said second section of said solid support comprises a second control band which comprises, in its turn, aliquots of heavy chains of a class of human immunoglobulins; with said class being selected from the group of heavy chains, $\mu$, $\gamma$ and $\alpha$, in relation to the class of antibodies which are to be determined by means of said diagnostic tool.

6. A diagnostic tool in accordance with claim 1, wherein said second section of said means of solid support comprises:

(i) A second control band comprising aliquots of the heavy $\mu$ chains;

(ii) A first recombinant protein which comprises a first region reproducing a sequence of amino acids corresponding to the sequence between aa540 and aa601, inclusive, read in the direction from the aminic end to the carboxylic end, of the viral protein p130, and at least one second region reproducing at least a portion of the sequence of amino acids of said exogenous protein;

(iii) A second recombinant protein which comprises a first region, reproducing a sequence of amino acids corresponding to the sequence between aa1144 and aa1233, inclusive, read in the direction from the aminic end to the carboxylic end, of the viral protein p130; and at least one second region reproducing at least a portion of the sequence of amino acids of said exogenous protein;

with said first and second recombinant proteins being positioned in at least one band, and said regions of said recombinant proteins capable of being positioned, one in relation to another, at different locations within each recombinant protein.

7. A diagnostic tool in accordance with claim 1, wherein said exogenous protein is CKS.

8. A diagnostic tool in accordance with claim 1, wherein said recombinant proteins comprise, in said regions, the entire amino acid sequence for each of the pp52, pp150, and p130, with said sequences of viral proteins being incorporated into the sequence of the CKS in a position which is immediately adjacent to the position aa171 of the latter.

9. A diagnostic tool in accordance with claim 1, wherein said means of solid support is a strip or a sheet of nitrocellulose on which the viral proteins (vp) and the recombinant proteins (rp) are positioned in accordance with a predetermined pattern.

10. A diagnostic tool in accordance with claim 1, wherein said predetermined pattern, whether of the viral proteins (vp) or of the recombinant proteins (rp), corresponds to the typical pattern of electrophoretic fractioning in polyacrylamide gel.

11. A diagnostic tool for the identification of direct anti-HCMV IgM's in the human serum, wherein said tool comprises, in combination, aliquots of the following:

Viral proteins vp150, vp82, vp65, vp38 and vp28, with said viral proteins being obtained from purified virions;

A plurality of recombinant proteins comprising immunogenic regions of the viral proteins pp150, pp52 and p130, with said regions being incorporated into CKS;

The CKS protein, by itself; and

The heavy $\mu$ chains of the human immunoglobulins; with said aliquots of said protein materials being supported by a means of solid support.

12. The diagnostic tool of claim 11, wherein said tool comprises a Western blot test for the identification of specific anti-HCMV antibodies in the human serum.

13. A method for the identification in the human serum of anti-HCMV IgM or IgG or IgA, or any combination of the foregoing, wherein said method comprises the phases of:

Purifying the virions of HCMV and separating from said purified virions at least the viral proteins vp150, vp82, vp65, vp38 and vp28;

Obtaining a plurality of recombinant proteins which are able to be expressed in a host organism, with said recombinant proteins comprising immunogenic regions of viral proteins, either structural or non-structural, and at least one region of an exogenous protein, which is able to be expressed in said organism; at least one of said immunogenic regions of the structural or non-structural viral proteins being selected for its capacity to stimulate specific immune responses in IgM or IgG or IgA, or any combination of the foregoing;

Placing on a means of solid support said viral proteins and said recombinant proteins, spaced from one another and positioned in accordance with a predetermined pattern;

Placing on said means of solid support said exogenous protein and the aliquots of the µ or γ or α heavy chains of the human immunoglobulins, or any combination of the foregoing, also spaced one from another and from said viral proteins and from said recombinant proteins;

Incubating said means of solid support, with said proteins and heavy chains of immunoglobulin being contained on said means of solid support, with the human serum which is to be analyzed and with a substance revealing the antibodies which are bound to the means of solid support;

Detecting the antibodies that have been bound to the means of solid support; and Comparing the consequent reaction with the viral proteins and with the recombinant proteins, considering the test to be positive only when at least one viral protein and at least one recombinant protein react with the serum under examination simultaneously, while said exogenous protein does not react with the serum and the heavy chain of immunoglobulin does react with the serum.

14. A recombinant protein material which is able to bind with the anti-HCMV IgM, comprising at least one of the two following recombinant proteins:

$$CKS_{(1-171aa)}\text{-}p130_{(540-601aa)}\text{-T-R-}CKS_{(171-260aa)}; \quad [2]$$

$$CKS_{(1-171aa)}\text{-}p130_{(1144-1233aa)}\text{-T-R-}CKS_{(171-260aa)}; \quad [3]$$

in which $CKS_{(1-171aa)}$ and $T\text{-R-}CKS_{(171-260aa)}$ represent the residues of the CKS protein of aa1 to aa171, respectively, inclusive, read in the direction from the aminic end to the carboxylic end, and from aa171 to aa260, inclusive, read in the direction from the aminic end to the carboxylic end; T and R are threonine and arginine, respectively; $p130_{(540-601aa)}$ represents the residue of the viral protein p130 from aa540 to aa601, inclusive, read in the direction from the aminic end to the carboxylic end; and $p130_{(1144-1233aa)}$ represents the residue of said viral protein p130 from aa1144 to aa1233, inclusive, read in the direction from the aminic end to the carboxylic end.

15. A diagnostic tool for the determination, by serological means, of the presence of the anti-HCMV antibodies, said tool comprising at least one diagnostic reagent comprising the recombinant protein material in accordance with in claim 14.

* * * * *